(12) United States Patent
Dunkel et al.

(10) Patent No.: US 10,406,314 B2
(45) Date of Patent: Sep. 10, 2019

(54) EXHALATION VALVE, INHALATION VALVE, VENTILATOR AND METHOD FOR CONTROLLING VENTILATION

(71) Applicant: Drägerwerk AG & Co. KGaA, Lübeck (DE)

(72) Inventors: Thorsten Dunkel, Fahrenkrug (DE); Andreas Junk, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 310 days.

(21) Appl. No.: 15/420,537

(22) Filed: Jan. 31, 2017

(65) Prior Publication Data
US 2017/0216554 A1    Aug. 3, 2017

(30) Foreign Application Priority Data
Feb. 3, 2016    (DE) .......................... 10 2016 001140

(51) Int. Cl.
*A61M 16/20*    (2006.01)
*A61M 16/00*    (2006.01)

(52) U.S. Cl.
CPC ........ *A61M 16/206* (2014.02); *A61M 16/204* (2014.02); *A61M 2016/0027* (2013.01); *A61M 2016/0039* (2013.01); *A61M 2205/42* (2013.01); *A61M 2205/50* (2013.01)

(58) Field of Classification Search
CPC ...... A61M 16/205–206; A61M 16/204; A61M 2016/0027; A61M 2016/0039; A61M 2205/42; A61M 2205/50; A61M 39/24; A61M 16/208; A61M 16/0468; A61M 16/06; A61M 15/0086; A41D 13/1138; F16K 15/16; A62B 9/02; A62B 18/10; A62B 9/022; B63C 11/2227

See application file for complete search history.

(56) References Cited

U.S. PATENT DOCUMENTS

| | | | | |
|---|---|---|---|---|
| 4,190,045 A | * | 2/1980 | Bartels ................. | A61M 16/20 128/205.24 |
| 4,454,893 A | * | 6/1984 | Orchard ............... | A61M 16/20 128/205.24 |
| 6,334,441 B1 | * | 1/2002 | Zowtiak ............ | A61M 16/0468 128/205.24 |

FOREIGN PATENT DOCUMENTS

DE    695 30 117 T2    12/2003

* cited by examiner

*Primary Examiner* — Manuel A Mendez
(74) *Attorney, Agent, or Firm* — McGlew and Tuttle, P.C.

(57) ABSTRACT

An exhalation valve, an inhalation valve, a ventilator and a method for controlling ventilation are provided. An exhalation valve (10) or inhalation valve (10) for a medical ventilator (30) for controlling a flow of a fluid, especially a breathing gas, has an inlet (12) and an outlet (14) for the fluid. Between the inlet (12) and the outlet (14), a valve seat crater (16) and a diaphragm (18) are provided. The diaphragm (18) is movable relative to the valve seat crater (16) for influencing the flow through the valve seat crater (16). The valve seat crater (16) and the diaphragm (18) are arranged such that the valve seat crater (16) can partially be sealed by means of the diaphragm (18), with the diaphragm (18) and the valve seat crater (16) not closing completely on initial contact of the diaphragm (18) and the valve seat crater (16).

20 Claims, 16 Drawing Sheets

EXHALATION VALVE, INHALATION VALVE, VENTILATOR AND METHOD FOR CONTROLLING VENTILATION

CROSS REFERENCE TO RELATED APPLICATIONS

This application claims the benefit of priority under 35 U.S.C. § 119 of German Application 10 2016 001140.8 filed Feb. 3, 2016, the entire contents of which are incorporated herein by reference.

FIELD OF THE INVENTION

The present invention pertains to an exhalation valve, to an inhalation valve, to a ventilator and to a method for controlling ventilation, and especially but not exclusively to a concept for an improved control of a valve for a ventilator.

BACKGROUND OF THE INVENTION

Valves and valve systems are used in the field of medicine and especially in automated patient supply. For example, diaphragms are employed in mechanical ventilation and are often indispensable elements there. A diaphragm is an elastic or partially elastic element or membrane, which can be acted on with a force or a displacement, by which force or displacement a deformation of the geometry becomes established. For example, an opening is closed or opened by the deformation.

Diaphragms are used, for example, in exhalation valves, and the respiratory phases of patients are controlled by means of them during active, mechanical ventilation. The diaphragm undergoes a great, dynamic change during the exhalation. The diaphragm is not infrequently induced to vibrate due to the controlling force and the opposing force of the gas mixture (also called "Durchfluss" in German or "flow" in English). These vibrations may have an adverse effect on the flow and pressure measurement through the ventilator. Furthermore, the comfort of the patient may be compromised by vibrations during the ventilation, or the vibrations may be so pronounced that they are in the audible range and are perceived as an acoustic nuisance for the user and the patient.

Vibrations, which may have an unfavorable effect, are often observed in existing systems in case of a high positive end-expiratory pressure (PEEP, positive residual pressure at the end of expiration).

SUMMARY OF THE INVENTION

Therefore, there is a need for developing an improved configuration for ventilating patients.

This need is met by exemplary embodiments of an exhalation valve or inhalation valve according to the invention, a ventilator according to the invention and a method according to the invention.

This is accomplished by using exhalation valves or inhalation valves (hereinafter also called valves for short) that make possible an improved control of the flow through more controlled opening and closing characteristics. Therefore, measures are taken on the valve, which measures permit complete opening, controllable or defined partial closing and complete closing, particularly, the valve includes means for complete opening, controllable or defined partial closing and complete closing. Exemplary embodiments can thus reduce the vibrations of the diaphragm, which develop, for example, due to an undefined closing of the "zero gap" (e.g., contact between a crater (also known a valve seat or valve seat crater) and a diaphragm) on one side and high local, flow-induced forces on the other side.

Therefore, exemplary embodiments create an exhalation valve or inhalation valve for a medical ventilator for controlling a flow of a fluid. The fluid is especially a breathing gas. The valve comprises an inlet and an outlet for the fluid. Between the inlet and the outlet, the valve has further a crater (also known as a valve seat or valve seat crater) and a diaphragm movable relative to the valve seat crater for influencing the flow through the valve seat crater. The valve seat crater and the diaphragm are arranged such that the valve seat crater can partially be sealed by means of the diaphragm, and the diaphragm and the valve seat crater are not closed all over during the initial contact. The non-allover closing and the partial sealability associated herewith can be used to stabilize the diaphragm position and to reduce vibrations. The valve seat crater can be sealed in a partially and fully controlled manner by means of the diaphragm in exemplary embodiments. Exemplary embodiments can thus make possible a full range of control, controlled opening, controlled partial opening or closing and controlled complete closing. This may lead to increased comfort especially in case of use in ventilators.

In exemplary embodiments, the diaphragm may have an elastic material and at least one damping element. The damping element may represent a simple structural measure in order to achieve the above-described controllability or partial closability. For example, the damping element may comprise a reinforcement of the diaphragm on one side. The reinforcement on one side can make possible a non-uniform yielding of the diaphragm and hence a controllable partial closing or opening. In some exemplary embodiments, the diaphragm and the valve seat crater may have a defined contact point or a defined, limited contact surface, at which or on which the diaphragm and the valve seat crater first touch one another during a closing of the valve. An opening and/or closing characteristic of a mechanical nature can thus be predefined by the defined contact point and the contact surface, and a flow characteristic will, in turn, become controllable based on the geometry of these opening and closing characteristics at given pressure differences.

In some exemplary embodiments, the valve seat crater may have a sealing contour for sealing with a sealing surface of the diaphragm. The valve seat crater and the diaphragm may be configured to form a sealing gap between the sealing contour and the sealing surface. The sealing gap may, in this case, be configured such that the sealing contour touches the sealing surface at a defined first point in the course of a closing and that the sealing gap assumes a defined dimension at a defined second point, at which the sealing contour and the sealing surface do not touch each other. Such an arrangement may likewise make possible a controllable behavior of the valve based on the corresponding geometric conditions. The flow of the fluid through the sealing gap can then be correspondingly controllable. In further exemplary embodiments, the diaphragm may have a lateral extension, for example, a diameter in case of a diaphragm with a lateral extension, for example, a diameter in case of a diaphragm with a round cross section, a semiaxis in case of an elliptical cross section, length or width in case of other shapes. When the sealing contour and the sealing surface touch each other at the defined first point, the dimension of the sealing gap at the defined second point may then exceed, for example, a percentage of the lateral extension of the diaphragm Due to such defined geometric conditions, exemplary embodiments can make it possible to infer other variables, for example, flowthrough, flow, volume flow, pressure, pressure difference, vibration intensity, vibration damping, etc., from a degree of opening or closing of the valve.

The damping element may be configured in other exemplary embodiments to deflect the diaphragm asymmetrically or symmetrically under the action of a force. The sealing surface can partially touch the sealing contour when the diaphragm partially seals the valve seat crater. In addition or as an alternative, the diaphragm may be configured such that an asymmetrical distribution of forces becomes established between the sealing surface and the sealing contour under the action of a force. The diaphragm can thus be controlled by corresponding means, e.g., pneumatically and/or by means of a plunger, and the asymmetrical deflection and/or force distribution then permits a corresponding control and/or vibration damping.

The diaphragm and the damping element may have a one-piece configuration in some exemplary embodiments. The damping element may now be arranged inside or outside the diaphragm, and many different possible applications and implementations are made possible hereby and exemplary embodiments can thus be adapted in this respect to the particular application. For example, the damping element may comprise an elastic structure and/or a compacted structure. The controllable partial closability can thus be achieved by means of corresponding structures. The sealing surface and the sealing contour may form an angle with one another. The oblique closing thus made possible may represent a simple implementation of the partial closability or opening of the valve. The sealing surface and/or the sealing contour may be beveled in relation to a longitudinal axis of the valve seat crater, which can lead to a similar effect and to a simple implementation.

In some exemplary embodiments, the sealing surface and/or the sealing contour may have one or more defined unevennesses, which form one or more defined residual openings between the sealing surface and the sealing contour when a predefined force acts on the diaphragm. The residual openings can then cause a defined flow, so that a controllable or defined state of the valve is achieved. The one or more residual openings can then be closable in some other exemplary embodiments by the action of another, stronger force on the diaphragm, so that the valve can then also be closed completely.

Moreover, exemplary embodiments provide a ventilator with an exhalation valve or inhalation valve according to the above description.

Exemplary embodiments also create a method for controlling ventilation by means of a flow of a fluid, especially of a breathing gas, through an exhalation valve or inhalation valve having an inlet and an outlet for the fluid. The valve has further, between the inlet and the outlet, a valve seat crater and a diaphragm movable relative to the valve seat crater for influencing the flow through the valve seat crater. The method for controlling the flow comprises a partial sealing of the valve seat crater with the diaphragm and a non-complete closing of the diaphragm and valve seat crater upon initial contact.

Further advantageous embodiments will be described in more detail below on the basis of the exemplary embodiments shown in the drawings, but, on the whole, the present invention is not limited, in general, to these exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
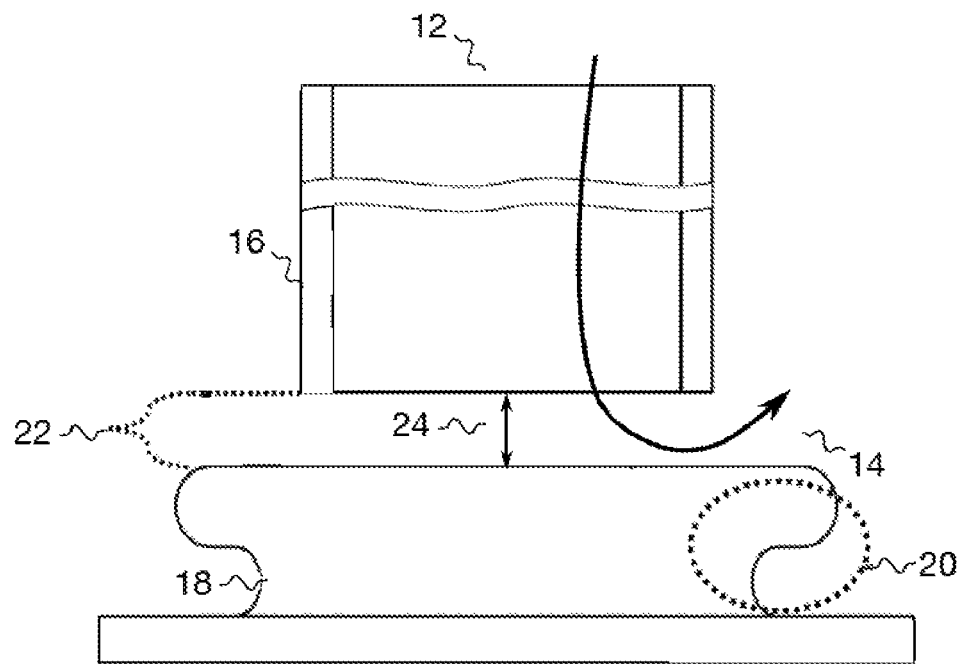
FIG. 1 is a schematic view showing an exemplary embodiment of an exhalation valve or inhalation valve.

Referring to the drawings, various exemplary embodiments will now be described in more detail with reference to the attached drawings, in which some exemplary embodiments are shown.

Identical reference numbers can designate identical or comparable components in the following description of the attached figures, which show only some exemplary embodiments. Further, summary reference numbers may be used for components and objects that appear several times in an exemplary embodiment or in a drawing, but are described together with respect to one or more features. Components or objects that are described with the same reference number or with a summary reference number may have an identical configuration but optionally also different configurations with respect to individual features, a plurality of features or all features, for example, their dimensioning, unless something different appears explicitly or implicitly from the description. Optional components are indicated by broken lines or arrows in the figures.

Even though exemplary embodiments may be modified and varied in different ways, exemplary embodiments are shown in the figures as examples and will be described herein in detail. It shall, however, be clarified that exemplary embodiments are not intended to be limited to the particular forms being disclosed, but exemplary embodiments shall rather cover all functional and/or structural modifications, equivalents and alternatives, which are within the scope of the present invention. Identical reference numbers designate identical or similar elements in the entire description of the figures.

It should be noted that an element that is referred to as being "connected" or "coupled" with another element may be connected or coupled directly with the other element or elements located in between may be present. If, by contrast, an element is referred to as being "directly connected" or "directly coupled" with another element, no elements located in between may be present. Other terms, which are used to describe the relation between elements should be interpreted in a similar manner (e.g., "between" versus "directly in between," "adjoining" versus "directly adjoining," etc.).

Unless specified otherwise, all the terms being used here (including technical and scientific terms) have the same meaning that is attached to them by a person of average skill in the field to which the exemplary embodiments belong. It shall further be clarified that terms, e.g., those that are defined in generally used dictionaries, are to be interpreted such that they have the meaning that is consistent with their meaning in the context of the relevant technique and are not to be interpreted in an idealized or excessively formal sense, unless this is expressly defined herein.

FIG. 1 shows an exemplary embodiment of an exhalation valve 10 or inhalation valve 10. The exhalation valve 10 or inhalation valve 10 shown in FIG. 1 is suitable, for example, for a medical ventilator for controlling a flow of a fluid, especially a breathing gas, which will be explained in more detail on the basis of the following figures. As is shown in FIG. 1, the valve 10 comprises an inlet 12 and an outlet 14 for the fluid. The flow direction may possibly also be different in exemplary embodiments and the inlet 12 and the outlet 14 are transposed in this case. The flow direction shown in FIG. 1 will be maintained in the following figures, but another flow direction or a transposition of the inlet and outlet is also possible.

Further, the valve 10 has, between the inlet 12 and the outlet 14, a valve seat (also referred to as a crater or valve seat crater) 16 and a diaphragm 18 movable relative to the valve seat crater for influencing the flow through the valve seat crater 16. The valve seat crater 16 and the diaphragm 18 are configured and arranged to provide an initial partial contact means wherein the valve seat crater 16 is partially sealed by the diaphragm 18, with the diaphragm 18 and the valve seat crater 16 not closing all over (not fully closing) during the initial contact. This incomplete closing can be achieved based on the different initial partial contact means explained in more detail below. For example, the initial partial contact means may be provided based on features in the area 20, which is shown in FIG. 1, and/or a sealing gap 22, which is located between the diaphragm 18 and the valve seat crater 16, may correspondingly be modified. A selection of concrete initial partial contact means features will be explained in detail below.

Figure 2:
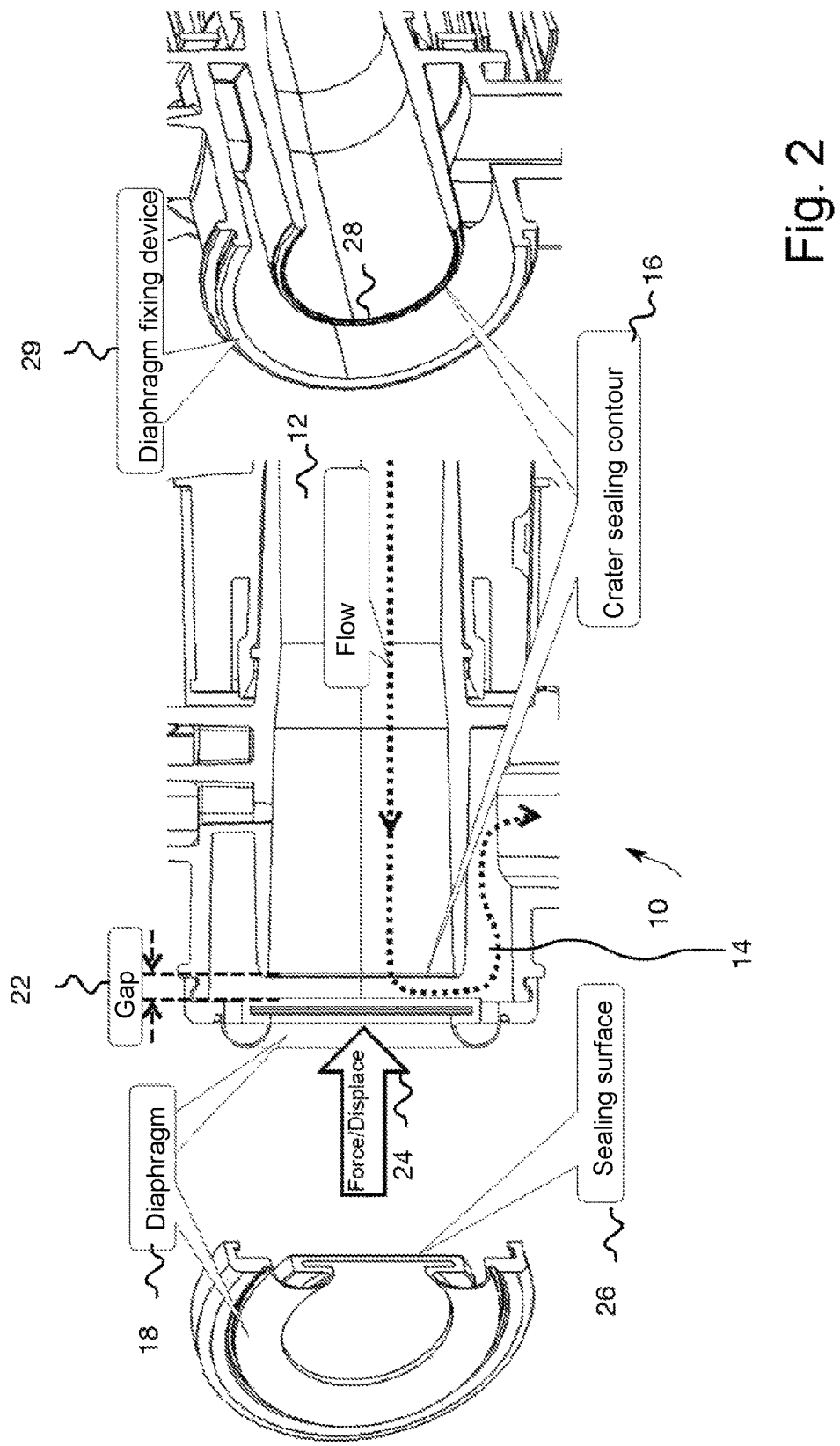
FIG. 2 is a sectional view of a valve in a ventilator.

FIG. 1 schematically shows the valve 10, in which the gap 22 between the diaphragm 18 and the valve seat crater 16 is still open. If the opposing force 24 acts on the diaphragm, the gap 22 becomes larger or smaller. The flow shown (volume flow of the breathing gas indicated by the bent arrow) can thus be dispensed in a smaller quantity and finally stopped altogether. The time and the rapidity of respiratory phases are thus controlled with the diaphragm 18 during mechanical ventilation and the value of the pressure level during the respiratory phases is controlled by varying the gap width. FIG. 2 shows an exemplary embodiment of an exhalation valve 10 or inhalation valve 10 as it can be used, for example, in a ventilator. FIG. 2 shows three views: a perspective view of a diaphragm 18 on the left-hand side, a sectional view of the valve 10 in the center and a perspective view of the corresponding valve seat crater 16 on the right-hand side. The sealing surface 26, which seals with a sealing contour 28 of the valve seat crater if a sufficient force 24 is applied to the diaphragm 18, can be seen in the view on the left-hand side. The diaphragm 18 has a disk-shaped configuration in this embodiment, and the sealing surface 26 is located in the center of the diaphragm 18 and is coupled with a fastening ring surrounding the diaphragm 18 concentrically via an elastic bead or a fold/hinge. The diaphragm 18 may be formed in one piece from an elastic material. These components are also shown in the center of FIG. 2, where the sealing gap 22 is open. The flow is shown by an arrow drawn in broken line and it extends in the view from right to left and then downward; consequently, the inlet 12 for the fluid is arranged on the right and the outlet 14 is arranged on the left in this exemplary embodiment. Moreover, the views in the center and on the right show fastening components of the valve seat crater 16, which are used for fastening in a ventilator, which will be explained below. The right side of FIG. 2 shows the valve seat crater 16, which has a fixing device 29 for the diaphragm 18, this fixing device being configured as a ring-shaped groove here. The valve seat crater 16 has a sleeve-like or cylindrical configuration, so that a circular sealing contour 28 is obtained.

Figure 3:
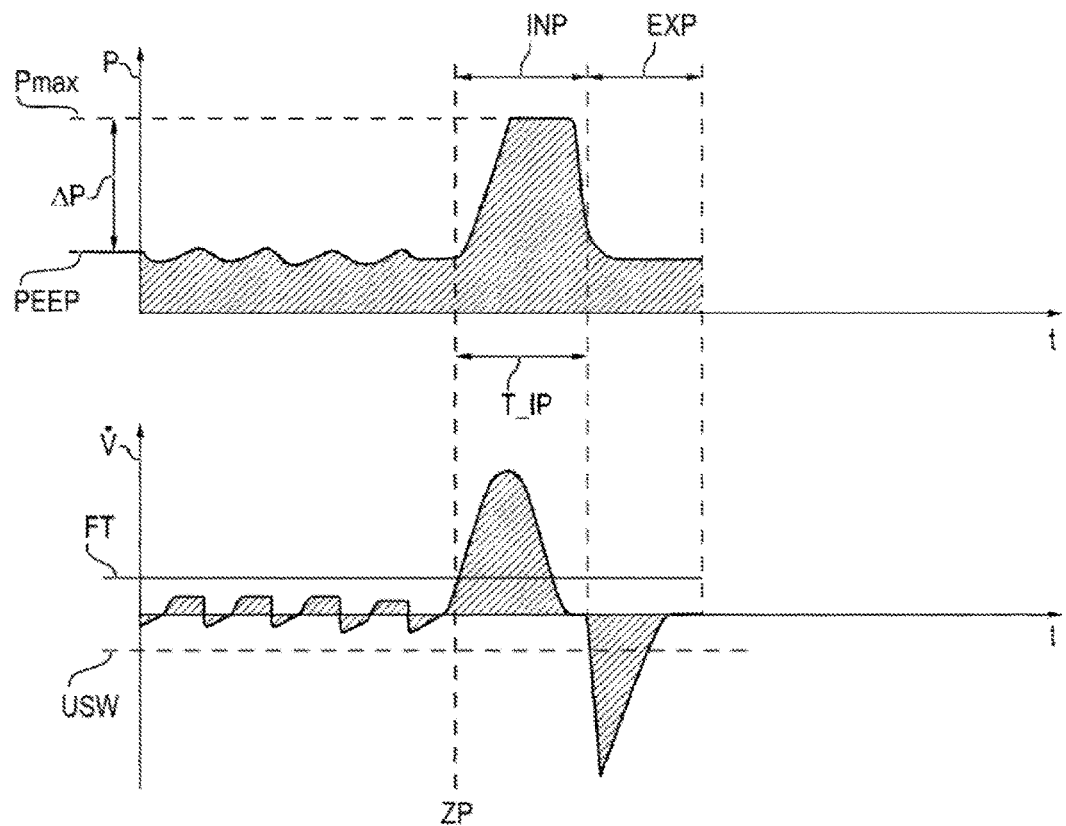
FIG. 3 is a pressure curve over time as well as a volume curve over time in the course of an inhalation and an exhalation.
Figure 4:
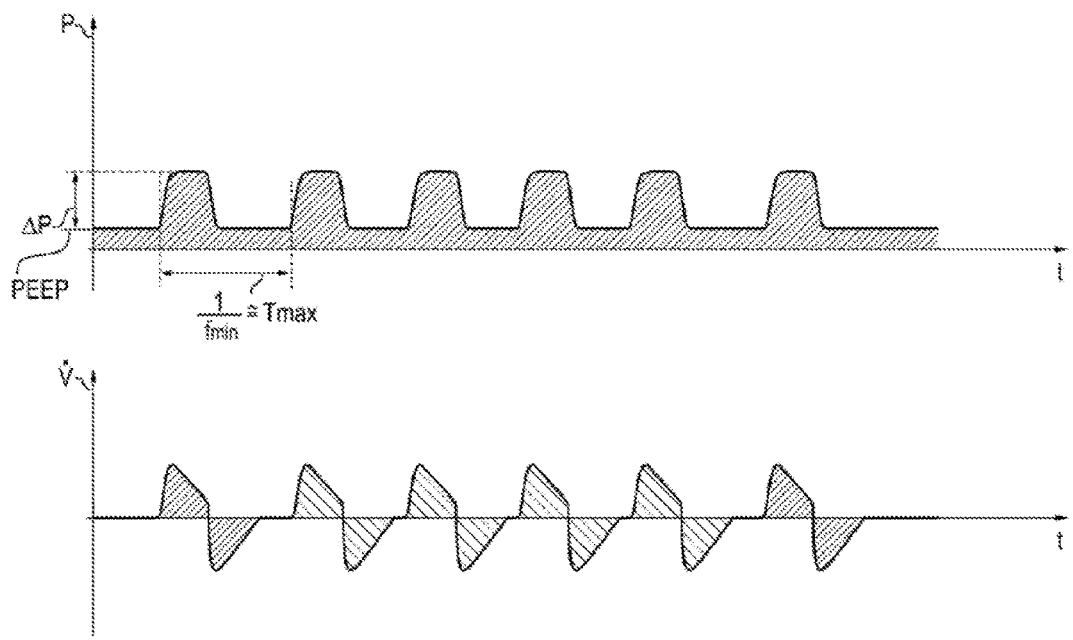
FIG. 4 is a pressure curve over time as well as a volume curve over time within the framework of a pressure-assisted ventilation, which takes place within the framework of spontaneous breathing attempts of a patient.
Figure 5:
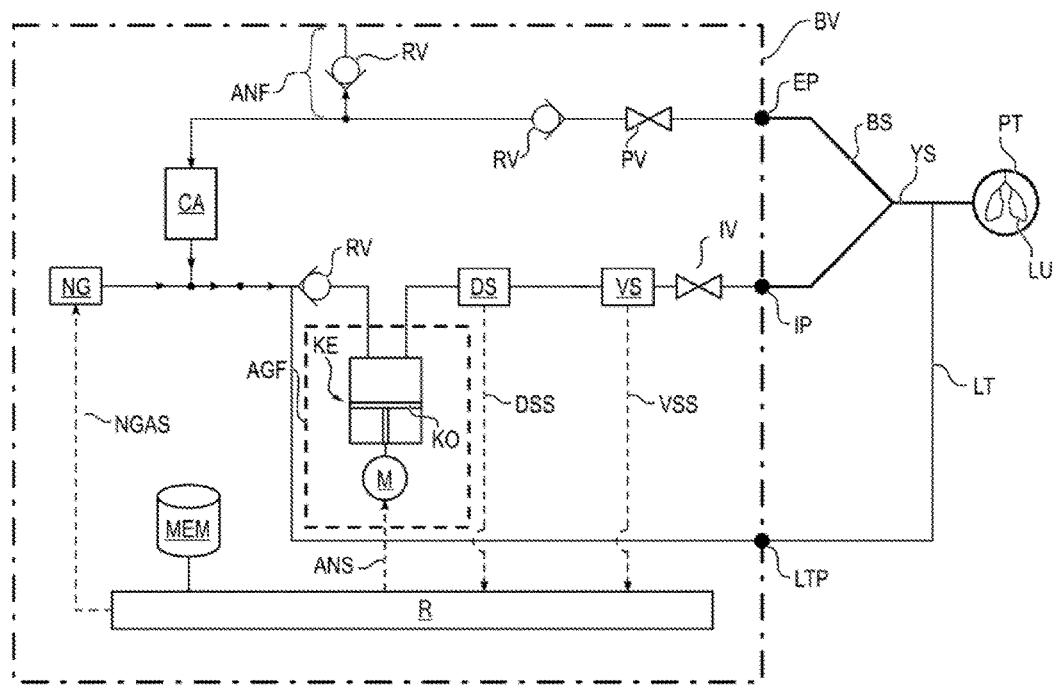
FIG. 5 is a schematic view showing an exemplary embodiment of a ventilator.

The course of ventilation as well as a ventilator shall be described in more detail based on the following FIGS. 3 through 5, using an exemplary embodiment of a valve. FIG. 3 shows a pressure curve over time as well as a volume flow curve over time in the course of an inhalation and an exhalation. FIG. 4 shows a pressure curve over time as well as a volume flow curve over time within the framework of pressure-assisted ventilation, which takes place in connection with spontaneous breathing attempts of a patient. FIGS. 3 and 4 show curves on the basis of which a pressure-controlled ventilation will be explained as an example.

To illustrate a ventilation with trigger control, FIG. 3 shows a pressure curve of a pressure value P over time, and a curve of a volume flow $\dot{V}$ over time can be seen as well. If a patient is ventilated by a ventilating device, the pressure is controlled such that the pressure is regulated before an inhalation phase INP to a minimum end-expiratory pressure PEEP (Positive End Expiratory Pressure in English). If the patient makes an attempt at breathing spontaneously, this leads to the volume flow $\dot{V}$ being exceeded based on a so-called trigger threshold or flow trigger threshold FT at the time ZP. If the threshold is exceeded, the pressure P is then adjusted such that the pressure P is adjusted to a maximum pressure Pmax, and this maximum pressure Pmax is above the minimum pressure PEEP by a differential pressure ΔP. A duration T_IP is usually preset for an inhalation phase, so that the exhalation phase EXP, during which pressure P is again lowered to the minimum pressure PEEP, is then started after the end of the duration T_IP. A negative volume flow V̇ is thus obtained during the exhalation phase based on the outflow of the volume flow V̇ from the patient.

Such a trigger-controlled ventilation is carried out, for example, within the framework of a pressure-assisted ventilation, as it is shown once again in FIG. 4.

FIG. 5 shows an exemplary embodiment of a ventilator 30 or of a ventilating device BV for the automated ventilation of a patient PT. The ventilating device BV has an inhalation port IP and an exhalation port EP, to which a ventilation tube BS, which faces the patient PT, can be connected. A breathing gas is fed to the patient via this ventilation tube BS and then removed from the patient towards the ventilating device BV. The feed takes place via the inhalation port IP and the removal via the exhalation port EP. The ventilation tube BS merges the connections of the ports EP, IP at a so-called Y-piece YS, which then usually ends at a tube, which is inserted into the patient PT in order to ventilate him via his lungs LU.

The ventilating device BV further has a breathing gas delivery unit AGF. The breathing gas delivery unit AGF is preferably a piston unit KE, in which a piston KO can be moved forward and backward by a motor M.

The ventilating device BV has at least one volume flow sensor VS to detect a volume flow of the breathing gas. The volume flow sensor VS can provide a volume flow signal VSS to a computer R. The computer R is at least one computer, which may also be embodied by a network of a plurality of computers. The ventilating device BV further has a pressure sensor DS for detecting a pressure of the breathing gas. The pressure sensor DS provides a pressure sensor signal DSS for the computer R. The computer R is configured to actuate the breathing gas delivery unit AGF via an actuating signal ANS. The computer R preferably accesses a memory unit MEM in order to carry out the method according to the present invention. A minimum pressure PEEP is preferably brought about by an exhalation valve PV, which corresponds to an exemplary embodiment of the valve 10 described and which is preferably located in the area of the exhalation port EP.

Further, there is an inhalation valve IV, which likewise corresponds to the valve 10 described, which controls the feed of breathing air from the ventilating device to the patient PT. In case the ventilating device BV is an anesthesia ventilating device, the ventilating device BV preferably has a carbon dioxide adsorber CA as well as an anesthetic gas mixing unit NG. A gas mixture necessary for the anesthesia can then be introduced into the breathing circuit via the anesthetic gas mixing unit NG. The ventilating device BV further has as the anesthesia ventilating device an anesthetic gas discharge line ANF and a connection to an anesthetic gas discharge line ANF. The gas flow within the ventilating device BV is controlled by nonreturn valves RV. The computer R preferably controls the anesthetic gas mixing unit NG by means of a control signal NGAS.

As is shown in FIGS. 3-5, there are inhalation and exhalation phases for the mechanical ventilation of a patient. The two phases can be controlled by inhalation valves and exhalation valves 10. Exemplary embodiments of the valves 10 reduce vibrations, which may occur in various situations and thus the valves 10 can favorably affect the patient's ventilation comfort. Vibrations may occur, for example, during the breathing air feed (inhalation) when the inhalation pressure plateau is reached or during the removal of breathing air (exhalation) when the end-expiratory pressure plateau (PEEP) is reached. Exemplary embodiments of the valves 10 may generally be used in ventilators, i.e., for example, in the area of anesthesia, intensive care and emergency ventilation. For example, the vibrations occurring can be distinguished according to frequency ranges of, for example, 0<f<20 Hz, 20 Hz<f<50 Hz, 50 Hz<f<200 Hz, 200 Hz<f<2 kHz, 2 kHz<f<20 kHz, and a plurality of frequencies may also occur simultaneously.

Some additional exemplary embodiments of valves, especially different configurations of the diaphragm 18 and of the valve seat crater 16, which may be adapted to one or more, optionally also all frequency ranges, will be described below. For example, the closing characteristic of the diaphragm 18 with respect to a first contact point on the valve seat crater 16 up to complete closing can be configured in a defined manner and vibrations can thus directly be reduced or entirely eliminated. The valve seat crater 16 can in this case be able to be sealed partially and completely in a controlled manner by means of the diaphragm 18. A plurality of options are conceivable for defining a first contact point, as this will schematically be shown in the following figures.

Figure 6:
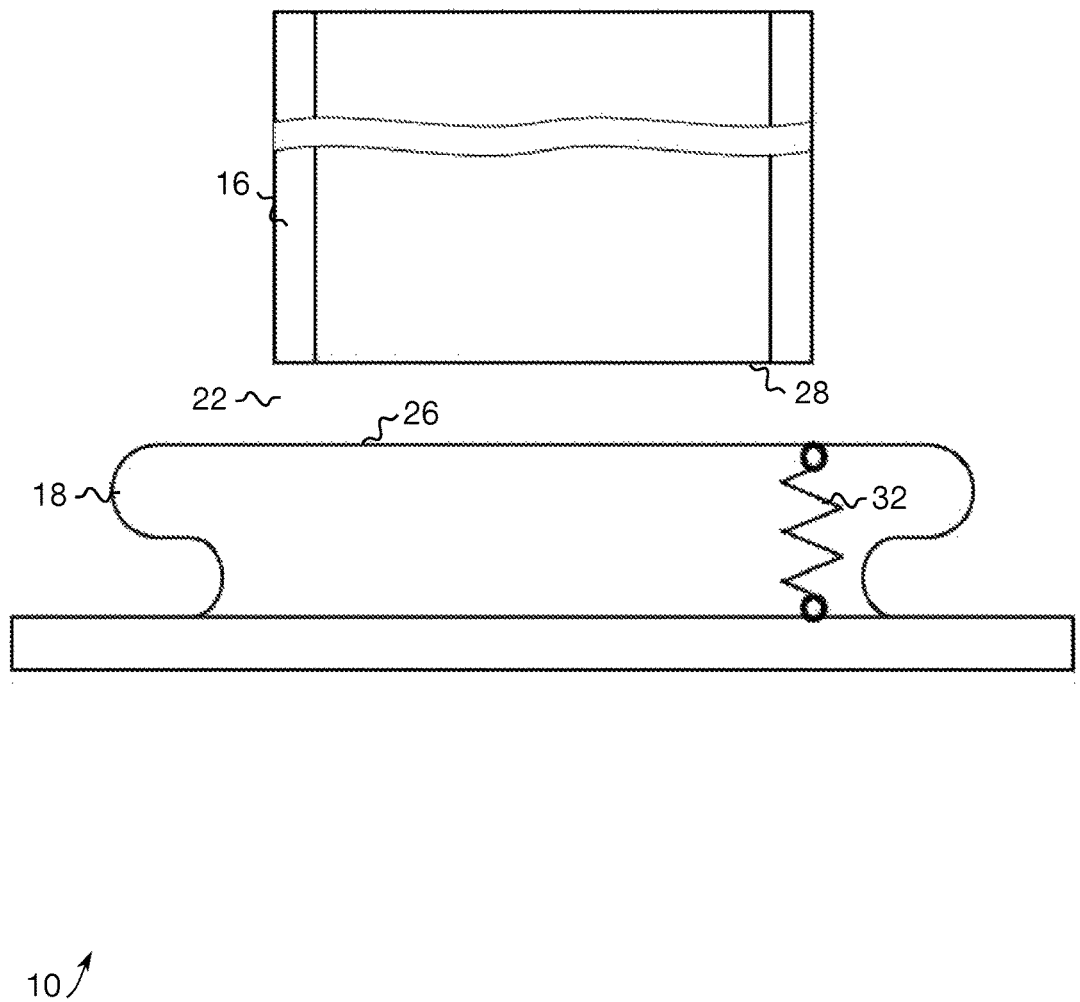
FIG. 6 is a schematic view showing an exemplary embodiment of an exhalation valve or inhalation valve with a reinforcement within the diaphragm.

FIG. 6 shows an exemplary embodiment of an exhalation valve 10 or inhalation valve 10 with a reinforcement within the diaphragm 18. The valve 10 may consequently comprise a damping element 32 and the diaphragm 18 may be formed from an elastic material. The damping element 32 may comprise, as is shown, for example, in FIG. 6, a reinforcement of the diaphragm 18 on one side. FIG. 6 further shows the sealing contour 28 of the valve seat crater 16, which faces the sealing surface 26 of the diaphragm 18.

Figure 7:
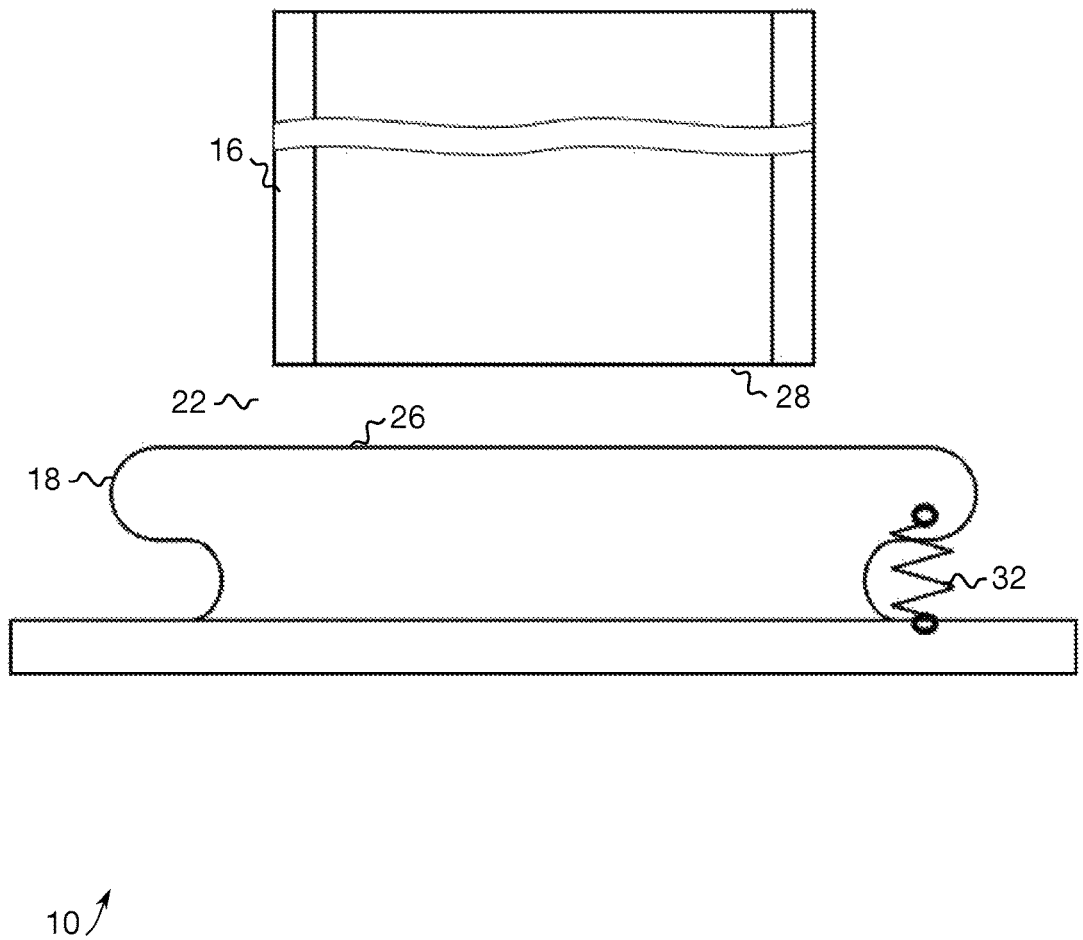
FIG. 7 is a schematic view showing an exemplary embodiment of an exhalation valve or inhalation valve with a reinforcement outside the diaphragm.

Diaphragm elastomers may generally be used as the material for the diaphragm 18 in exemplary embodiments. Examples are hyperelastic materials, most of which are approved for medical applications (biocompatibility), e.g., silicones and thermoplastic elastomers (TPE). For example, metals approved for medical applications or plastics approved for medical applications, e.g., titanium, brass, polypropylene (PP), polyethylene (PE), poly(aryl)sulfone (PSU), acrylonitrile-butadiene-styrene (ABS), polystyrene (PS), etc., may be used for the damping element 32 and the diaphragm reinforcement. For example, plastics approved for medical applications or metals approved for medical applications, e.g., PP, PE, PSU, ABS, PS, titanium, brass, etc., may be used for the valve seat crater 16. FIG. 6 shows the damping element within the diaphragm 18, FIG. 7 shows an exemplary embodiment of an exhalation valve 10 or inhalation valve 10 with a reinforcement or with a damping element 32 outside the diaphragm 18. Another exemplary embodiment of an exhalation valve 10 or inhalation valve 10 with a reinforcement or with a damping element 32 outside the diaphragm 18 is shown in FIG. 8.

Figure 8:
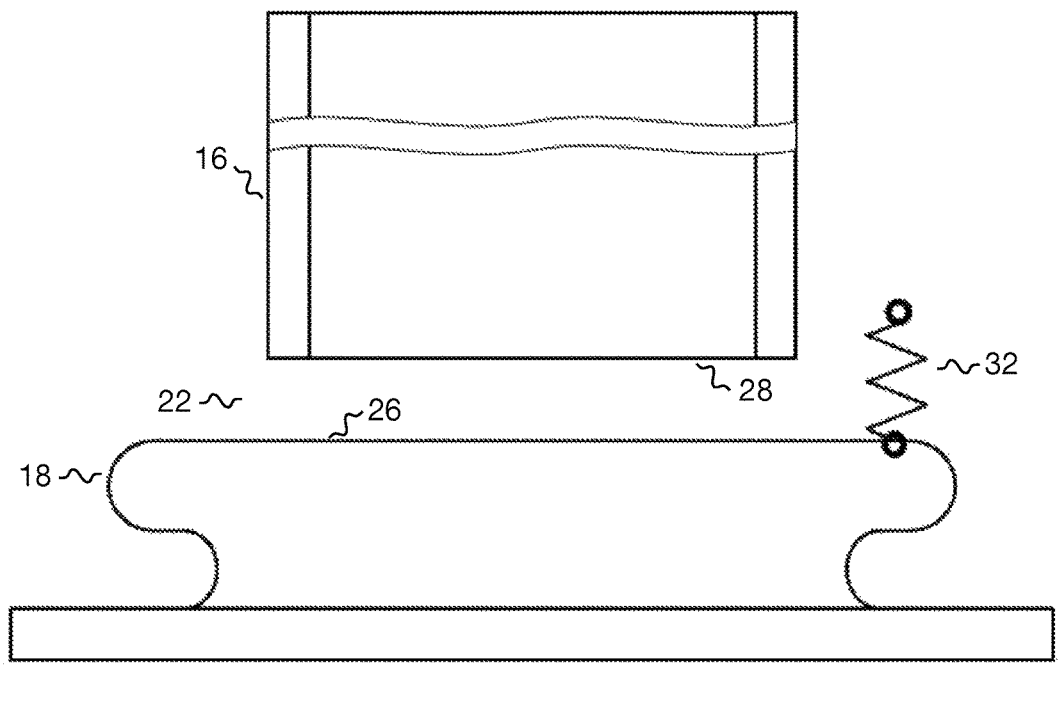
FIG. 8 is a schematic view showing another exemplary embodiment of an exhalation valve or inhalation valve with a reinforcement outside the diaphragm.
Figure 9:
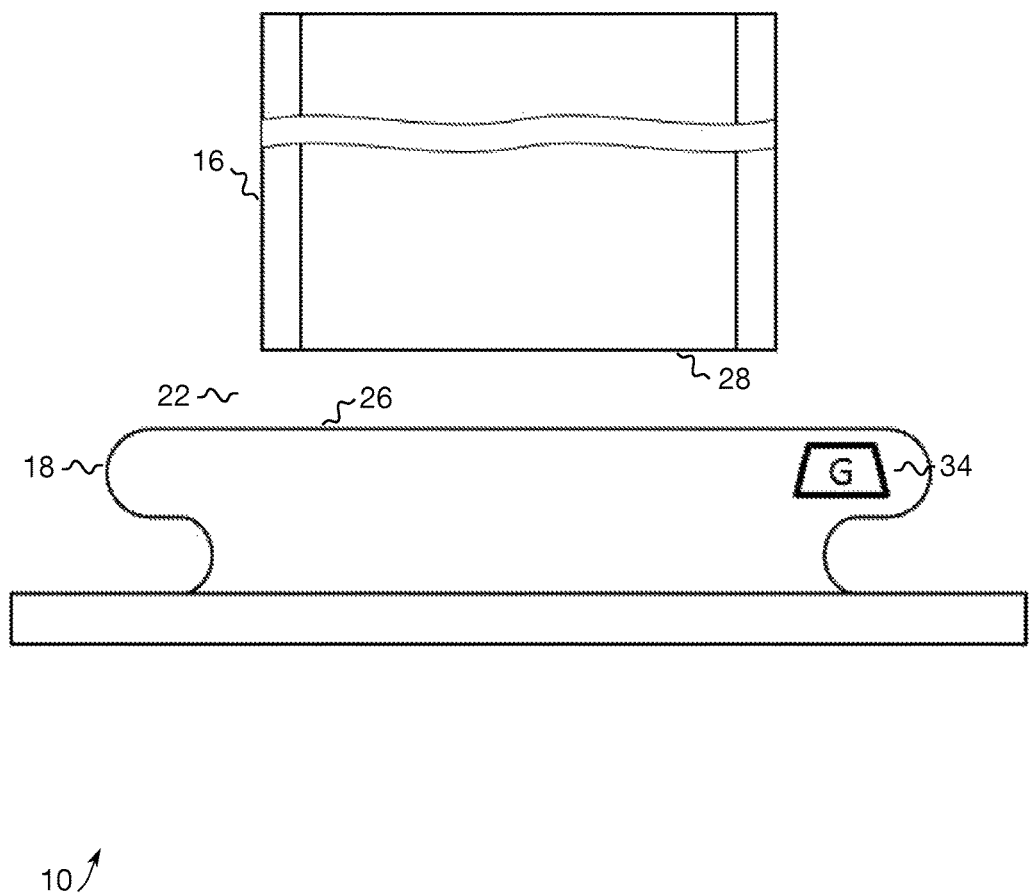
FIG. 9 is a schematic view showing an exemplary embodiment of an exhalation valve or inhalation valve with a reinforcement or weighting of the diaphragm on one side.
Figure 10:
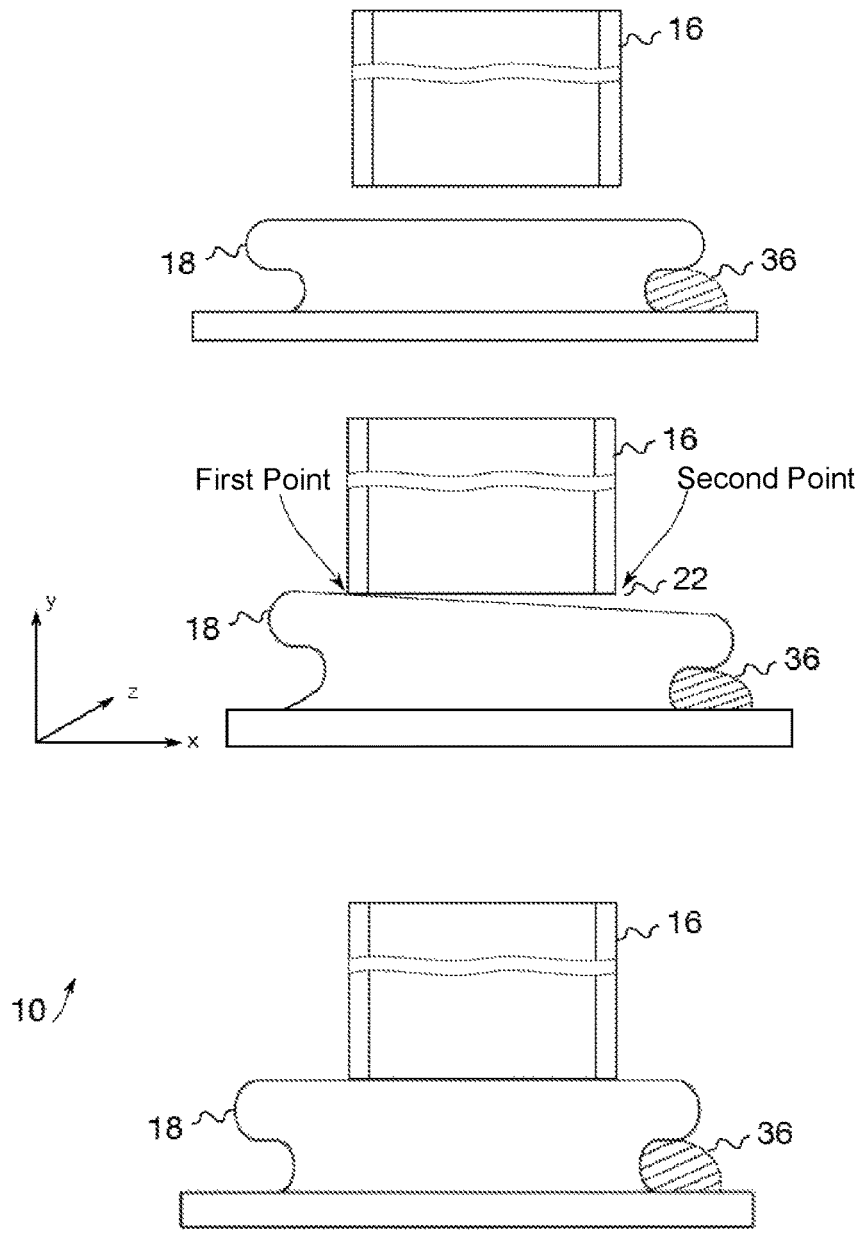
FIG. 10 is a schematic view showing a hinge principle in some exemplary embodiments.

The damping element 32 is shown in FIGS. 6-8 in a simplified manner as a spring symbol, which may, in turn, correspond to different implementations in exemplary embodiments. Examples are ribs, webs, straps, compactions, thickenings, which may each be formed from the same material or a material other than the material of the diaphragm 18. FIG. 9 shows an exemplary embodiment of an exhalation valve 10 or inhalation valve 10 with a compaction or weighting 34 of the diaphragm on one side. In the exemplary embodiments according to FIGS. 6-9, the damping elements 32 or the weighting 34 lead to a static/dynamic change in the angle of the axes of rotation of the valve seat crater 16 and the diaphragm 18 during the operation. A kind of hinge is formed. This hinge principle shall be explained in more detail for some exemplary embodiments on the basis of FIG. 10. FIG. 10 shows a closing operation of the valve 10 in one exemplary embodiment in a characteristic sequence: Open—partially closed—completely closed. Not all reference numbers are repeated again in FIG. 10 for the sake of clarity; the components shown correspond to those in the other figures.

The valve 10 is shown in the opened state in the top part of FIG. 10. FIG. 10 shows in the center that during the closing operation, the diaphragm 18 and the valve seat crater 16 form a defined contact point or a defined limited contact surface, at or on which the diaphragm 18 and the valve seat crater 16 will first touch one another during the closing of the valve 10. The view in the bottom part of FIG. 10 now shows the valve 10 in the completely closed state. The asymmetry shown in the center of FIG. 10 can be achieved, for example, by the above-described damping elements 32 or the weighting 34.

As was already explained on the basis of the above-described views, the valve seat crater 16 has a sealing contour 28 for sealing with a sealing surface 26 of the diaphragm 18. The valve seat crater 16 and the diaphragm 18 are configured in this case to form a sealing gap 22 between the sealing contour 28 and the sealing surface 26. The sealing gap 22 is configured, in turn, such that when the sealing contour 28 and the sealing surface 26 touch each other and the sealing gap 22 is consequently closed at a defined first point (on the left in the view shown in the center of FIG. 10), the sealing gap 22 assumes a defined dimension at a defined second point (on the right in the view shown in the center of FIG. 10), at which the sealing contour 28 and the sealing surface 26 do not touch each other. In some other exemplary embodiments, the flow of the fluid through the sealing gap 22 thus becomes able to be controlled. In other words, the sealing gap 22 is formed such that the sealing contour 28 touches the sealing surface 26 at a defined first point in the course of the closing of the sealing gap 22, and that the sealing gap 22 assumes a defined dimension at a defined second point, at which the sealing contour 28 and the sealing surface 26 do not touch each other.

The controllability is thus linked with the geometry of the diaphragm 18. The diaphragm 18 may have a lateral extension and the dimension of the sealing gap 22 at the defined second point may exceed a percentage of the lateral extension of the diaphragm 18 when the sealing contour 28 and the sealing surface 26 touch each other at a defined first point. The diaphragm 18 is assumed to have a round cross section in FIG. 10, so that the height of the gap at the second point in the view shown in the center is greater than a percentage of the diameter of the diaphragm 18. In other exemplary embodiments, the residual gap is, for example, at least 1% of the valve seat crater diameter. Larger initial gap dimensions, e.g., 2%, 3%, 5%, 10%, 20%, etc., are, however, likewise conceivable. An absolute value, e.g., 0.1 mm, 0.2 mm, 1 mm, 2 mm, 5 mm, 10 mm, etc., is also possible in other exemplary embodiments, Returning to the exemplary embodiments shown in FIGS. 6-9, it is possible to use as a damping element 32, for example, a reinforcement of the internal diaphragm geometry (FIG. 6), reinforcement of the external diaphragm geometry (FIGS. 7 and 8), external damping of the diaphragm displacement (FIG. 8), as well as an asymmetric change in the diaphragm weight (FIG. 9). This will lead to a change in the angle of the axes of rotation of the valve seat crater 16 and diaphragm 18 on actuation. The diaphragm 18 may now be heavier on one side or at a point, for example, due to accumulation of material and external application of material. FIG. 10 thus shows an exemplary embodiment in which the damping 32 is formed to asymmetrically deflect the diaphragm 18 upon application of a force. The sealing surface 26 partially touches the sealing contour 28 when the diaphragm 18 partially seals the valve seat crater 16. The diaphragm 18 is configured such that an asymmetric distribution of forces becomes established between the sealing surface 26 and the sealing contour 28 when a force is applied to the diaphragm 18. The force may be applied with various means or mechanisms in exemplary embodiments, examples being pneumatic, electromechanical, mechanical (e.g., plunger), fluid mechanical-pneumatic, fluid mechanical-(electro)mechanical means or mechanisms, etc.

In another exemplary embodiment, the diaphragm 18 and the damping element 32 are made in one piece, for example, by compaction of material on one side of the diaphragm 18.

The damping element 32 is arranged within or outside the diaphragm. In general, the damping element 32 may comprise an elastic structure and/or a compacted structure. The possibility of reinforcing the external diaphragm geometry on one side by one or more ribs 36 in the displacement path may be implemented as another exemplary embodiment. Ribs 36 are provided for this, for example, in the area 20, compare FIG. 1, as this is indicated by broken lines in FIG. 10. It is conceivable to provide only one rib 36, which will thus define the above-described second point. However, a plurality of ribs are also conceivable, and they are arranged along the circumference of the diaphragm 18 and the characteristic shown in FIG. 10 is thus obtained as an end result. Webs, straps, brackets, which may be formed in one piece or also as multipart components, are also conceivable as an alternative to the ribs.

The characteristic resulting herefrom is similar, in principle, to that of a cover with a hinge, which can move only about the hinge axis during opening and closing. As is shown in the center of FIG. 10, the reinforcement 36 acts as a fixed point, which suppresses the motion in the X direction and markedly limits same in the Z direction. A slight motion is still possible at the fixed point itself in the Y direction (right-hand side of the view in FIG. 10), whereas the greatest and fastest displacements are possible on the opposite side (left-hand side of the view in FIG. 10).

If the entire diaphragm 18 shall in this case form a seal on the valve seat crater 16, the diaphragm 18 and the valve seat crater 16 touch each other at the beginning of the closing operation at first on the surfaces on which the diaphragm 18 has the highest degrees of freedom, namely, opposite the fixed point or at the first point in FIG. 10. The rest of the diaphragm 18 follows with a short time delay. A concrete contact point (first point) with defined closing characteristics can thus be obtained on the valve seat crater 16 and the vibration is suppressed or reduced. FIG. 10 thus shows an improved or optimized closing operation. The opened diaphragm 18 is shown in the upper view, for example, in the inoperative state. In the view shown in the center, the diaphragm 18 touches the valve seat crater 16 in a defined manner. It then closes further, until it comes fully to lie on the valve seat crater 16, as this is shown in the bottom part of FIG. 10. The indicated rib may likewise be configured as an elastic rib.

Figure 11:
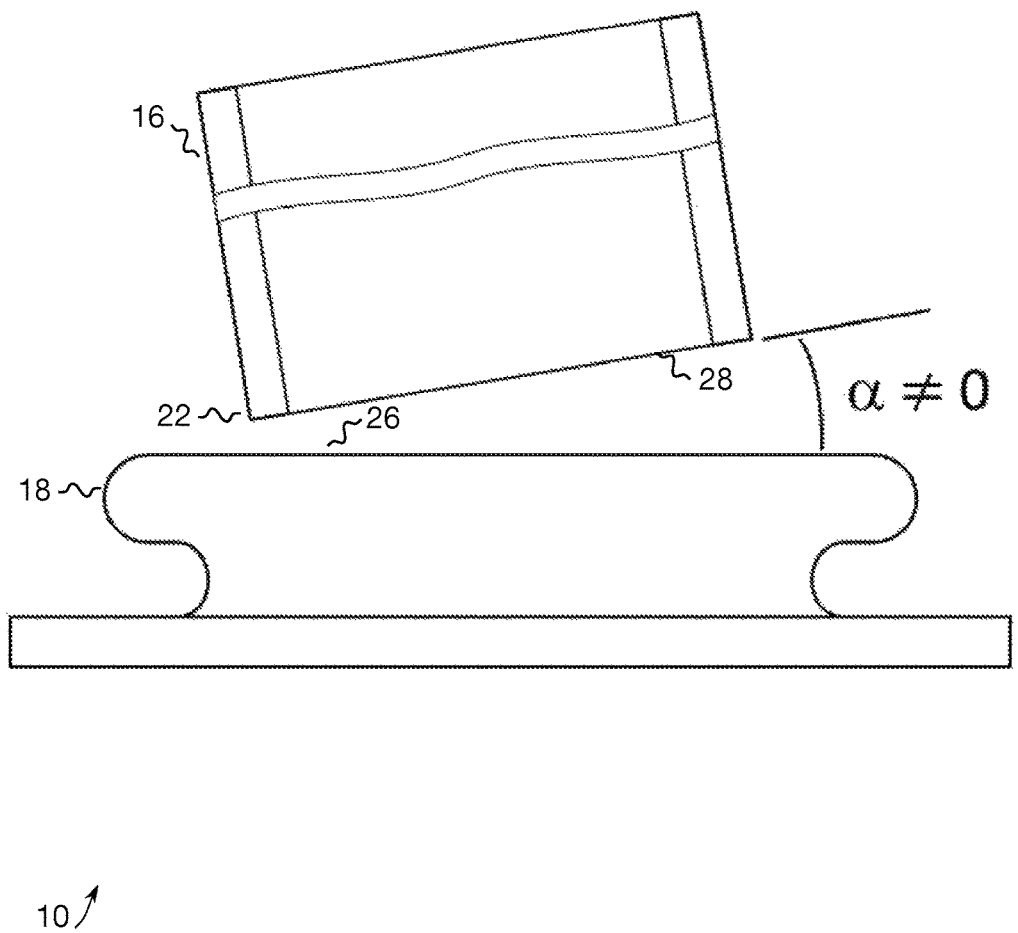
FIG. 11 is a schematic view showing an exemplary embodiment of an exhalation valve or inhalation valve with an angle between the diaphragm and the valve seat crater.
Figure 12:
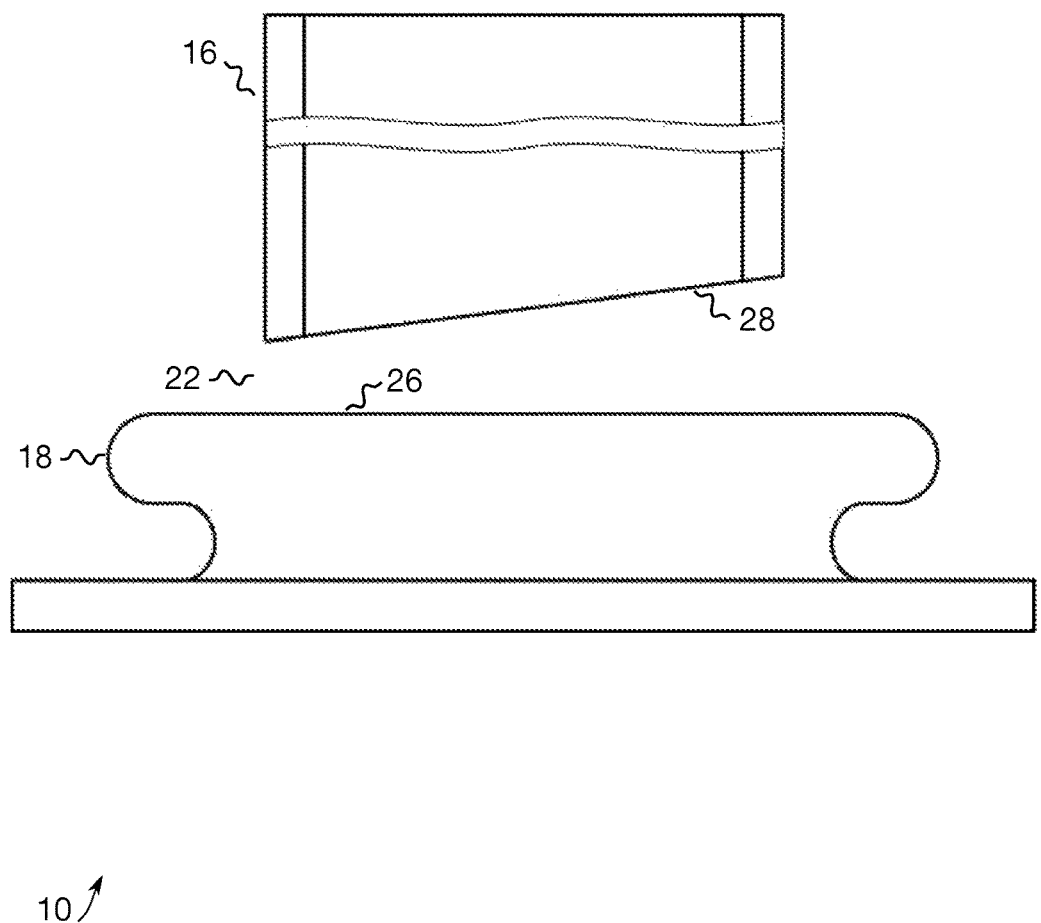
FIG. 12 is a schematic view showing an exemplary embodiment of an exhalation valve or inhalation valve with a beveled valve seat crater.
Figure 13:
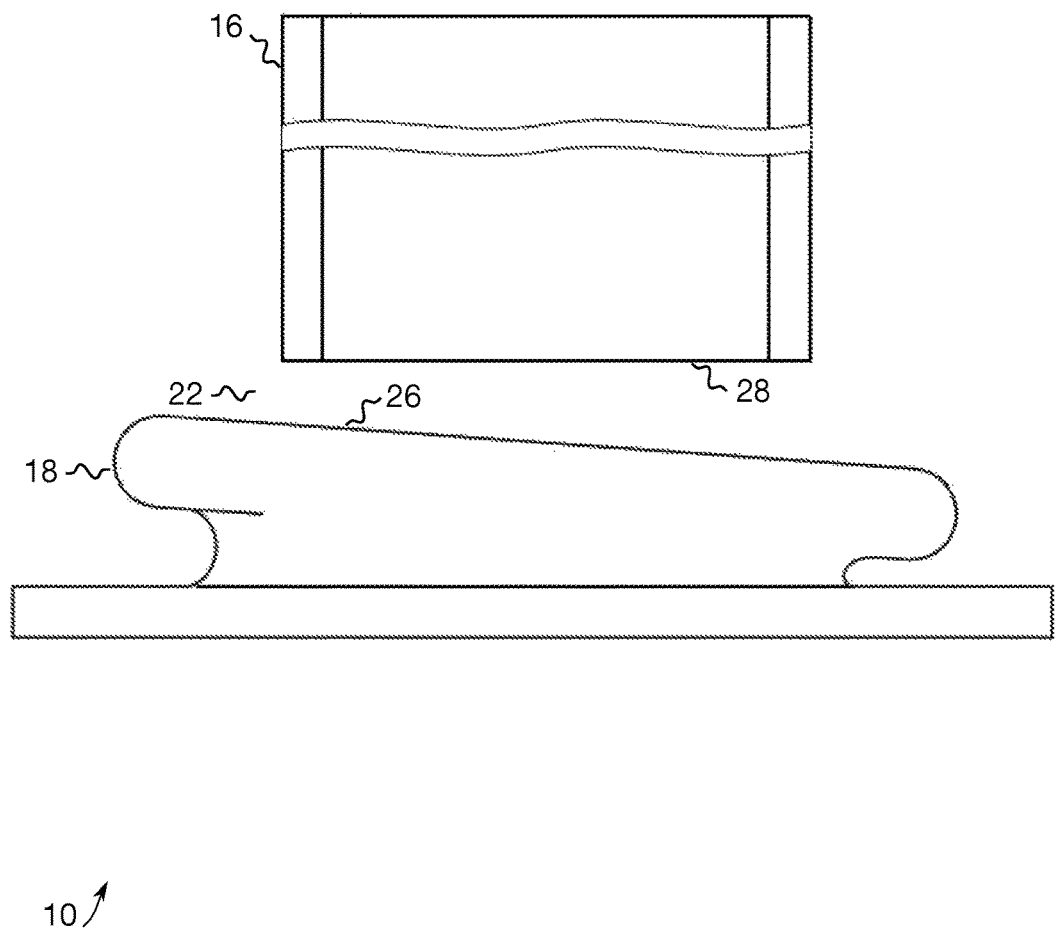
FIG. 13 is a schematic view showing an exemplary embodiment of an exhalation valve or inhalation valve with a beveled diaphragm.

The effect shown in FIG. 10 can also be achieved by other measures in other exemplary embodiments. For example, a change in the angle of the axes of rotation of the valve seat crater 16 and diaphragm 18 in the static state can be used by varying the valve seat crater 16. FIG. 11 shows an exemplary embodiment of an exhalation valve 10 or inhalation valve 10 with an angle α different from zero between the diaphragm 18 and the valve seat crater 16. The diaphragm 18 and the valve seat crater 16 are located opposite each other at an angle >0°, so that a closing characteristic similar to that in FIG. 10 is obtained. The sealing surface 26 and the sealing contour 28 form an angle with one another. FIG. 12 shows an exemplary embodiment of an exhalation valve 10 or inhalation valve 10 with a beveled valve seat crater 16. The valve seat crater 16 is beveled opposite the diaphragm 18. The inclination does not have to be linear. FIG. 13 shows an exemplary embodiment of an exhalation valve 10 or inhalation valve 10 with a beveled or shortened diaphragm 18. Consequently, variations of the diaphragm geometry and/or of the valve seat crater geometry can be embodied in exemplary embodiments. The diaphragm 18 is, for example, shortened on one side. The displacement until closing continues to be made possible by the elasticity of the diaphragm 18, compare FIG. 13. The sealing surface 26 and/or the sealing contour 28 is beveled here in relation to the longitudinal axis of the valve seat crater 16. Beveling both components is likewise conceivable.

Figure 14:
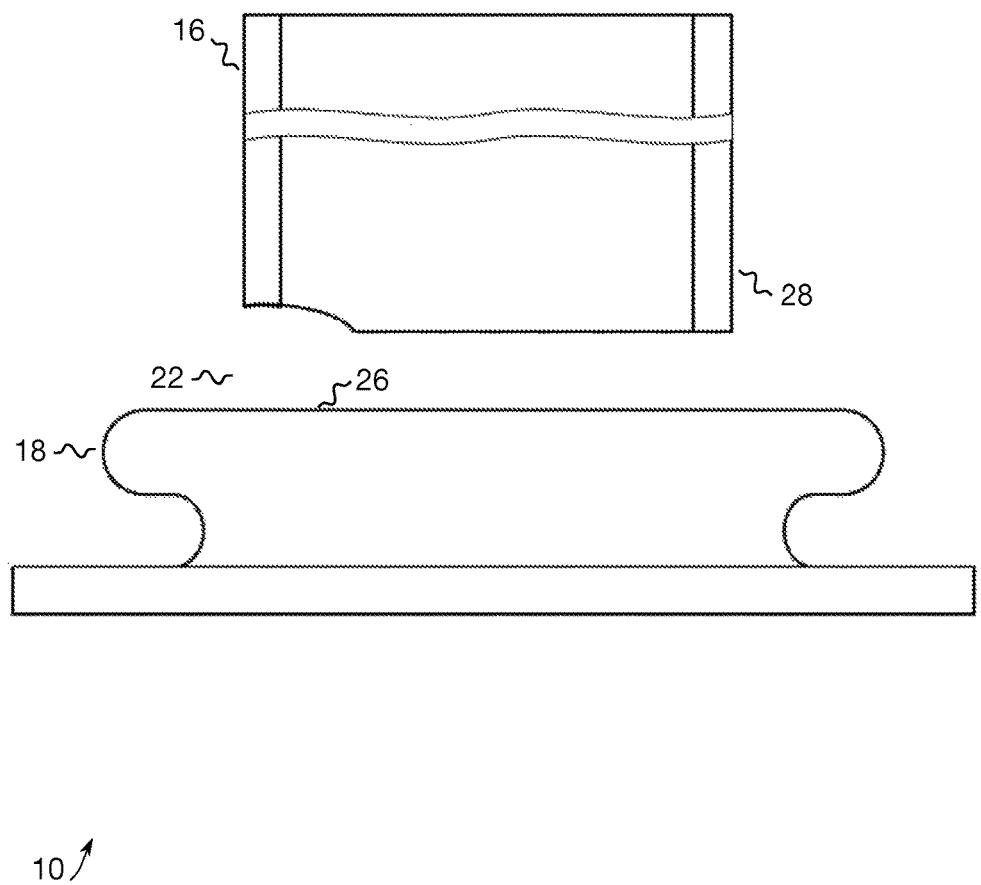
FIG. 14 is a schematic view showing an exemplary embodiment of an exhalation valve or inhalation valve with a defined unevenness in the valve seat crater.
Figure 15:
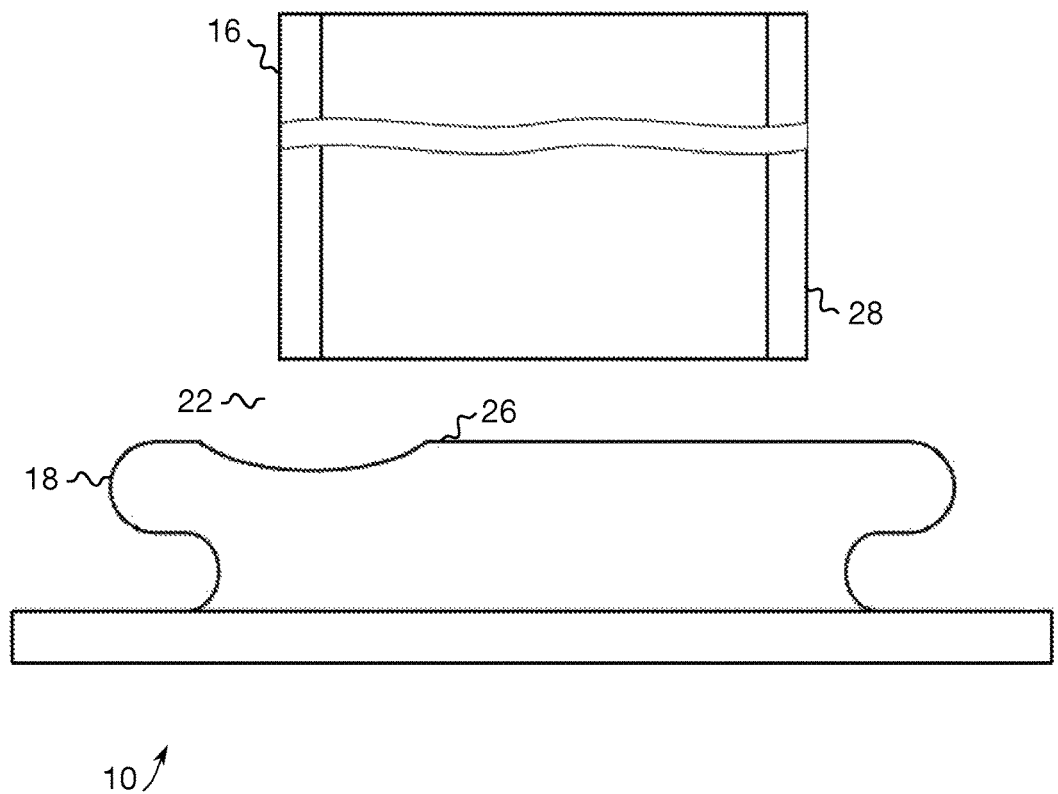
FIG. 15 is a schematic view showing an exemplary embodiment of an exhalation valve or inhalation valve with a defined unevenness in the diaphragm.

FIG. 14 shows an exemplary embodiment of an exhalation valve 10 or inhalation valve 10 with a defined unevenness in the valve seat crater 16. This defined unevenness may correspond to a defined or also asymmetric recess, deformation, bulge, structure in the diaphragm and/or valve seat crater surface, so that the sealing gap does not close completely on initial contact between the diaphragm 18 and the valve seat crater 16, but there remains a defined residual gap or a residual opening. The size of the residual opening may correspond, for example, to more than 1%, 2%, 3%, 5%, 10%, 20%, 30%, 50% of the diaphragm or valve seat crater surface. FIG. 15 shows an exemplary embodiment of an exhalation valve 10 or inhalation valve 10 with a defined unevenness in the diaphragm 18. Such unevennesses or recesses may be used additionally or as an alternative in additional exemplary embodiments. The valve seat crater 16 may be provided with a recess on one side, FIG. 14, in order to guarantee a defined residual opening in a flatly closed valve 10. As the closing force/closing displacement increases further, this residual gap can be closed in a specific manner. The sealing surface 26 of the diaphragm 18 may be provided with a recess on one side in order to guarantee a defined residual opening in a flatly closed valve 10. This residual gap can be closed in a specific manner as the closing force/closing displacement increases further. The sealing surface 26 and/or the sealing contour 28 may consequently have one or more defined unevennesses in other exemplary embodiments, and these unevennesses form one or more defined residual openings between the sealing surface 26 and the sealing contour 28 when a predefined force acts on the diaphragm 18. The one or more residual openings can then be able to be closed when an additional, stronger force acts on the diaphragm 18.

Figure 16:
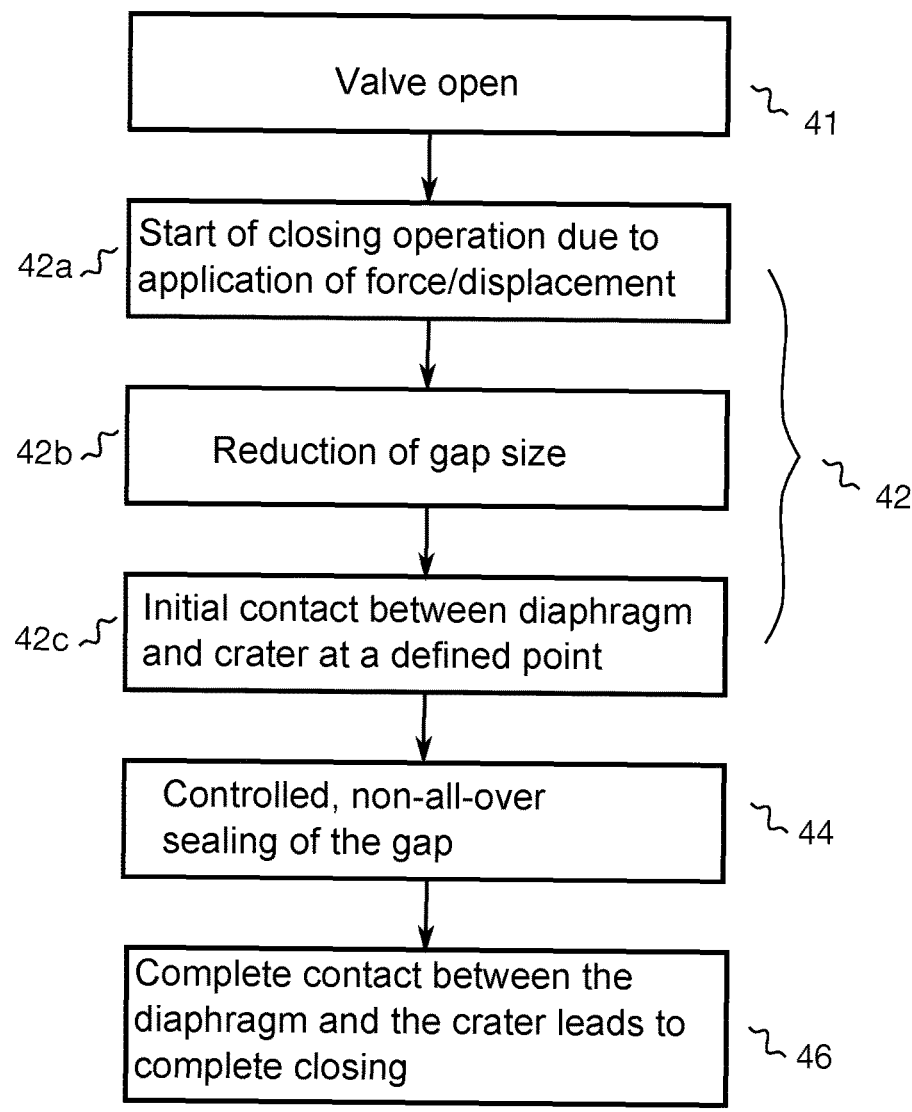
FIG. 16 is a block diagram of a flow chart of an exemplary embodiment of a method for controlling ventilation.

FIG. 16 shows a block diagram of a flow chart of an exemplary embodiment of a method for controlling ventilation. The control is effected by means of a flow, through an exhalation valve 10 or inhalation valve 10 having an inlet 12 and an outlet 14 for the fluid, especially a breathing gas, according to the above description, especially FIG. 1. The valve 10 further comprises between the inlet 12 and the outlet 14 a valve seat crater 16 and a diaphragm 18 movable relative to the valve seat crater for influencing the flow through the valve seat crater 16. The method for controlling the flow comprises a partial sealing 42 of the valve seat crater 16 with the diaphragm 18 and a closing 44 of the diaphragm 18 and valve seat crater 16, which closing does not occur over the entire area, on initial contact. As is shown in FIG. 16, the process being shown here begins with an open valve 10 in step 41. The partial sealing 42 is divided here into three substeps, namely, the start of the closing process by the application of force/displacement 42a, the subsequent reduction of the gap size 42b and the initial contact between the diaphragm 18 and the valve seat crater 16 at a defined point. This is then followed by a controlled sealing 44 of the gap, which does not take place over the entire area. Full contact is then achieved in a next step between the diaphragm 18 and the valve seat crater 16, which leads to complete sealing of the valve 10. The valve 10 can then be opened analogously in the reverse order.

In summary, the susceptibility to vibration can be reduced and the frequency range of the vibrations can be shifted in at least some exemplary embodiments by an asymmetric distribution of the material hardness and/or of the elasticity of the material of the diaphragm 18 or by asymmetrically changing the displacement path of the diaphragm 18. The embodiment with defined recess in the valve seat crater-valve assembly unit guarantees that the opening of the valve always takes place in a defined controllable and regulatable manner (in the direction of "zero gap") even in case of a high PEEP pressure during the closing of the diaphragm.

The features disclosed in the above description, in the claims and in the drawings may be significant for the implementation of exemplary embodiments in their different configurations both individually and in any combination and, unless it appears otherwise from the description, they may be combined with one another as desired.

Even though some aspects were described in connection with a device, it is apparent that these aspects also represent a description of the corresponding method, so that a block or a component of a device should also be considered to be a corresponding method step or as a feature of a method step. Analogously hereto, aspects that were described in connection with a method step or as a method step also represent a description of a corresponding block or detail or feature of a corresponding device.

The above-described exemplary embodiments represent only an illustration of the principles of the present invention. It is apparent that modifications and variations of the devices and details described here will be apparent to other persons skilled in the art. The present invention is therefore intended to be limited only by the scope of protection of the following patent claims rather than by the specific details, which were presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

APPENDIX: LIST OF REFERENCE CHARACTERS

10 Valve
12 Inlet
14 Outlet
16 Valve seat crater
18 Diaphragm
20 Area
20 Area
22 Sealing gap
24 Force
26 Sealing surface
28 Sealing contour 29 Fixing device
30 Ventilator
32 Damping element
34 Weighting
36 Reinforcement
41, 42, 42a, 42b, 42c, 44, 46 Steps
AGF Breathing gas delivery unit
ANF Anesthetic gas discharge line
ANS Actuating signal
BS Ventilation tube
BV Ventilating device
CA Carbon dioxide adsorber
DS Pressure sensor
DSS Pressure sensor signal
EP Exhalation port
EXP Exhalation phase
FT Trigger threshold
INP Inhalation phase
IP Inhalation port
IV Inhalation valve
KE Piston unit
KO Piston
LU Lungs
M Motor
MEM Memory unit
NG Anesthetic gas mixing unit
NGAS Control signal
P Pressure
PEEP Minimum pressure
Pmax Maximum pressure
PT Patient
PV Exhalation valve
R Computer
RV Nonreturn valve
T_IP Duration
Volume flow
VS Volume flow sensor
VSS Volume flow sensor signal
YS Y-piece
ZP Time
ΔP Differential pressure

What is claimed is:

1. A medical ventilator exhalation valve or medical ventilator inhalation valve for controlling a medical ventilator flow of a fluid, the valve comprising:
   an inlet;
   an outlet;
   a valve seat crater; and
   a diaphragm, the valve seat crater and the diaphragm being disposed between the inlet and the outlet, wherein the diaphragm is movable relative to the valve seat crater for influencing the flow through the valve seat crater, wherein the valve seat crater and the diaphragm are arranged such that the valve seat crater is at least initially only partially sealed by the diaphragm, wherein the diaphragm and the valve seat crater do not close completely on initial contact between the diaphragm and the valve seat crater, diaphragm comprising an elastic material and at least one damping element.

2. A medical ventilator exhalation valve or medical ventilator inhalation valve in accordance with claim 1, wherein the valve seat crater is partially or completely sealed by the diaphragm and the partial or complete sealing by the diaphragm is controlled.

3. A medical ventilator exhalation valve or medical ventilator inhalation valve in accordance with claim 1, wherein the damping element comprises a reinforcement of the diaphragm on one side.

4. A medical ventilator exhalation valve or medical ventilator inhalation valve in accordance with claim 1, wherein the diaphragm and the valve seat crater have a defined contact point or a defined limited contact surface, at or on which the diaphragm and the valve seat crater first touch one another during the closing of the valve.

5. A medical ventilator exhalation valve or medical ventilator inhalation valve in accordance with claim 1, wherein:
   the valve seat crater has a sealing contour for sealing with a sealing surface of the diaphragm;
   the valve seat crater and the diaphragm are configured to form a sealing gap between the sealing contour and the sealing surface;
   the sealing gap is formed such that the sealing contour touches the sealing surface at a defined first point during the closing of the sealing gap; and
   the sealing gap assumes a defined dimension at a defined second point, at which the sealing contour and the sealing surface do not touch each other.

6. A medical ventilator exhalation valve or medical ventilator inhalation valve in accordance with claim 5, wherein the flow of the fluid through the sealing gap can be controlled.

7. A medical ventilator exhalation valve or medical ventilator inhalation valve in accordance with claim 5, wherein:
   the diaphragm has a lateral extension; and
   the dimension of the sealing gap at the defined second point exceeds 1 percent of the lateral extension of the diaphragm upon the sealing contour initially touching the sealing surface at the defined first point.

8. A medical ventilator exhalation valve or medical ventilator inhalation valve in accordance with claim 1, wherein:
   the valve seat crater has a sealing contour for sealing with a sealing surface of the diaphragm;
   the damping element is configured to asymmetrically deflect the diaphragm under the action of a force;
   the sealing surface partially touches the sealing contour when the diaphragm partially seals the valve seat crater or the diaphragm is configured such that an asymmetric distribution of forces becomes established between the sealing surface and the sealing contour when a force acts on the diaphragm or both the sealing surface partially touches the sealing contour when the diaphragm partially seals the valve seat crater and the diaphragm is configured such that an asymmetric distribution of forces becomes established between the sealing surface and the sealing contour when a force acts on the diaphragm.

9. A medical ventilator exhalation valve or medical ventilator inhalation valve in accordance with claim 1, wherein:
   the diaphragm and the damping element are configured in one piece;
   the damping element is arranged on either side of the diaphragm;
   the damping element comprises an elastic structure or the damping element comprises a compacted structure or the damping element comprises both an elastic structure and a compacted structure.

10. A medical ventilator exhalation valve or medical ventilator inhalation valve in accordance with claim 1, wherein the valve seat crater and the diaphragm are disposed and mounted to form an initial partial contact means for the initial contact between the diaphragm and the valve seat crater such that the valve seat crater is at least initially only partially sealed by the diaphragm.

11. A medical ventilator exhalation valve or medical ventilator inhalation valve in accordance with claim 1, wherein:
the diaphragm has a sealing surface movably mounted relative to the valve seat crater between a first position and a second position for controlling a flow through the valve seat crater, the first position of the sealing surface being spaced from the valve seat crater, the second position being configured to have the sealing surface in contact with the valve seat crater and block the flow through the valve seat crater;
the valve seat crater and the sealing surface are configured to initially only partially seal the valve seat crater by the diaphragm;
the valve seat crater has a first section and a diametrically opposite second section;
the diaphragm is movably mounted relative to the valve seat crater along a displacement path between the first and second positions for controlling a flow through the valve seat crater;
the damping element is arranged in the displacement path, the damping element being configured to cause asymmetrical movement of the diaphragm along the displacement path, the damping element and the asymmetrical movement being configured to cause the diaphragm to consistently first contact the first section of the valve seat crater before contacting the second section of the valve seat crater when the diaphragm closes the flow through the valve seat crater.

12. A medical ventilator valve in accordance with claim 11, wherein:
the diaphragm has an area adjacent the sealing surface and arranged radially outward from the sealing surface;
the diaphragm has a fastening ring concentrically surrounding the sealing surface via the area;
the damping element is arranged in the area.

13. A medical ventilator valve in accordance with claim 12, wherein:
the area is elastic.

14. A medical ventilator valve in accordance with claim 12, wherein:
the area is an elastic bead.

15. A medical ventilator valve in accordance with claim 12, wherein:
the area is a fold.

16. A ventilator with a medical ventilator exhalation valve or medical ventilator inhalation valve comprising:
an inlet;
an outlet;
a valve seat crater;
a diaphragm, the valve seat crater and the diaphragm being disposed between the inlet and the outlet, wherein the diaphragm is movable relative to the valve seat crater for influencing the flow through the valve seat crater, wherein the valve seat crater and the diaphragm are arranged such that the valve seat crater is at least initially only partially sealed by the diaphragm, wherein the diaphragm and the valve seat crater do not close completely on initial contact between the diaphragm and the valve seat crater; the diaphragm comprising an elastic material and at least one damping element.

17. A ventilator in accordance with claim 16, wherein the valve seat crater and the diaphragm are disposed and mounted to form an initial partial contact means for the initial contact between the diaphragm and the valve seat crater such that the valve seat crater is at least initially only partially sealed by the diaphragm.

18. A method for controlling ventilation by controlling a flow of a breathing gas through an exhalation valve or through an inhalation valve or through both an exhalation valve and an inhalation valve, the method comprising the steps of:
providing a valve comprising an inlet, an outlet, a valve seat crater and a diaphragm, with the valve seat crater and the diaphragm being disposed between the inlet and the outlet, with the diaphragm movable in relation to the valve seat crater for influencing the flow through the valve seat crater; and
partially closing the valve seat crater with the diaphragm, which is not an all-over closing, on initial contact, the diaphragm comprising an elastic material and at least one damping element.

19. A method according to claim 18, wherein the step of partially closing comprises:
starting of the partially closing with an application of force to the diaphragm or with a displacement of the diaphragm to reduce a gap between the diaphragm and the valve seat crater;
providing an initial contact between the diaphragm and the valve seat crater at a defined point; and
controlling a non-all-over sealing of the gap.

20. A method according to claim 19, further comprising completely closing the valve seat crater with the diaphragm with a complete contact between the diaphragm and the vale seat crater leading to the complete closing.

* * * * *